(12) United States Patent
Latham et al.

(10) Patent No.: US 9,644,066 B2
(45) Date of Patent: May 9, 2017

(54) CYCLIC AMINE COMPOUNDS, COMPOSITIONS, AND POLYURETHANE FOAMS MADE THEREFROM

(71) Applicant: Dow Global Technologies LLC, Midland, MI (US)

(72) Inventors: Dwight D. Latham, Clute, TX (US); Phillip S. Athey, Lake Jackson, TX (US); Stephen W. King, League City, TX (US)

(73) Assignee: DOW GLOBAL TECHNOLOGIES LLC, Midland, MI (US)

( * ) Notice: Subject to any disclaimer, the term of this patent is extended or adjusted under 35 U.S.C. 154(b) by 58 days.

(21) Appl. No.: 14/369,631

(22) PCT Filed: Dec. 28, 2012

(86) PCT No.: PCT/US2012/072095
§ 371 (c)(1),
(2) Date: Jun. 27, 2014

(87) PCT Pub. No.: WO2013/102097
PCT Pub. Date: Jul. 4, 2013

(65) Prior Publication Data
US 2015/0005404 A1    Jan. 1, 2015

Related U.S. Application Data

(60) Provisional application No. 61/717,913, filed on Oct. 24, 2012, provisional application No. 61/581,323, filed on Dec. 29, 2011.

(51) Int. Cl.
| | | |
|---|---|---|
| C08G 18/20 | (2006.01) | |
| C07D 295/13 | (2006.01) | |
| C08G 18/48 | (2006.01) | |
| C08G 18/76 | (2006.01) | |
| C08G 18/08 | (2006.01) | |
| C08G 18/32 | (2006.01) | |
| C08G 18/18 | (2006.01) | |
| C08J 9/14 | (2006.01) | |
| C08G 101/00 | (2006.01) | |

(52) U.S. Cl.
CPC ....... *C08G 18/2081* (2013.01); *C07D 295/13* (2013.01); *C08G 18/14* (2013.01); *C08G 18/2027* (2013.01); *C08G 18/3218* (2013.01); *C08G 18/4816* (2013.01); *C08G 18/4829* (2013.01); *C08G 18/4841* (2013.01); *C08G 18/7657* (2013.01); *C08G 18/7664* (2013.01); *C08J 9/144* (2013.01); *C08J 9/146* (2013.01); *C08G 18/18* (2013.01); *C08G 2101/00* (2013.01); *C08G 2101/005* (2013.01); *C08G 2101/0083* (2013.01); *C08J 2375/08* (2013.01)

(58) Field of Classification Search
CPC .... C08G 18/14; C08G 18/18; C08G 18/2027; C08G 18/2081
See application file for complete search history.

(56) References Cited

U.S. PATENT DOCUMENTS

| | | | |
|---|---|---|---|
| 4,568,746 A | 2/1986 | Cowherd, III | |
| 4,863,890 A | 9/1989 | Köll | |
| 4,973,692 A | 11/1990 | Burgess et al. | |
| 4,977,266 A | 12/1990 | Burgess et al. | |
| 4,992,587 A | 2/1991 | Köll | |
| 5,196,588 A | 3/1993 | Burgess et al. | |
| 5,256,786 A | 10/1993 | Bowman et al. | |
| 5,362,700 A | 11/1994 | Doumaux, Jr. | |
| 5,410,086 A | 4/1995 | Burgess | |
| 6,307,102 B1 * | 10/2001 | Tokumoto .......... | C08G 18/1875 544/404 |
| 6,465,601 B1 | 10/2002 | Wiesendanger et al. | |
| 6,534,441 B1 | 3/2003 | Bartley et al. | |
| 7,053,247 B2 | 5/2006 | Lif et al. | |
| 8,187,997 B2 | 5/2012 | King et al. | |
| 8,188,318 B2 | 5/2012 | Petraitis et al. | |
| 8,293,676 B2 | 10/2012 | King et al. | |
| 8,367,870 B2 | 2/2013 | Burdeniuc et al. | |
| 8,383,861 B2 | 2/2013 | Do et al. | |
| 2003/0032553 A1 | 2/2003 | Wendel et al. | |
| 2008/0004362 A1 | 1/2008 | Masuda et al. | |
| 2008/0090922 A1 | 4/2008 | Vedage et al. | |
| 2008/0132725 A1 | 6/2008 | Melder et al. | |
| 2010/0087683 A1 | 4/2010 | Cook et al. | |
| 2010/0094007 A1 | 4/2010 | King et al. | |
| 2010/0216361 A1 | 8/2010 | Bruchmann et al. | |
| 2010/0305228 A1 | 12/2010 | Gossner et al. | |
| 2010/0324261 A1 | 12/2010 | Muelhaupt et al. | |
| 2014/0357750 A1 | 12/2014 | King et al. | |
| 2015/0011762 A1 | 1/2015 | King | |

FOREIGN PATENT DOCUMENTS

| | | |
|---|---|---|
| EP | 0 412 611 | 2/1991 |
| EP | 0 414 574 | 2/1991 |
| EP | 0 737 669 | 10/1996 |
| GB | 1508460 | 4/1978 |
| GB | 1551127 | 8/1979 |
| WO | WO 96/38226 | 12/1996 |
| WO | 2004/060956 A1 | 7/2004 |
| WO | 2010008675 A1 | 1/2010 |
| WO | WO 2010/042157 | 4/2010 |
| WO | 2012006548 A1 | 1/2012 |
| WO | WO 2013/101345 | 7/2013 |
| WO | WO 2013/102053 | 7/2013 |

OTHER PUBLICATIONS

Bazzicalupi, C., et al., (1998) *Reinforced piperazine rings containing polyamines: metal complex equilibria and structural studies, Inorganica Chimica Acta* 268: 63-68.

(Continued)

*Primary Examiner* — Melissa Rioja
(74) *Attorney, Agent, or Firm* — Kagan Binder, PLLC

(57) ABSTRACT

The present invention describes cyclic amine compounds useful for catalysts for polyurethane form-forming compositions. The cyclic amine compounds of the invention provide distinct benefits for reaction compositions, methods, and polyurethane foams based on their desirable physical and catalytic properties.

14 Claims, No Drawings

(56) References Cited

OTHER PUBLICATIONS

Marchand, A.P., et al., (2004) *Synthesis and Electrospray Ionization Mass Spectrometric Evaluation of the Metal Cation Complexation Behavior of Cage-Annulated Azacrown Ethers*, Heterocycles 62: 279-296.

* cited by examiner

CYCLIC AMINE COMPOUNDS, COMPOSITIONS, AND POLYURETHANE FOAMS MADE THEREFROM

This application claims benefit from International Application No. PCT/US2012/072095 which was filed on Dec. 28, 2012, which in turn claims priority to U.S. Provisional Patent Application Ser. No. 61/717,913 filed Oct. 24, 2012; and U.S. Provisional Patent Application Ser. No. 61/581,323 filed Dec. 29, 2011, the disclosures of which are incorporated herein by reference.

PRIORITY CLAIM

This application claims the benefit of U.S. Provisional Application Ser. No. 61/581,323, filed Dec. 29, 2011, entitled "FORMATION OF HIGHER MOLECULAR WEIGHT CYCLIC POLYAMINE COMPOUNDS FROM CYCLIC POLYAMINE COMPOUNDS" and U.S. Provisional Application Ser. No. 61/717,913, filed Oct. 24, 2012, entitled "CYCLIC AMINE COMPOUNDS, COMPOSITIONS, AND POLYURETHANE FOAMS MADE THEREFROM", which applications are incorporated herein by reference in their entirety.

FIELD

The present invention pertains to cyclic amines and compositions containing cyclic amines, as well as polyurethane foams prepared from the cyclic amines.

BACKGROUND

Polyurethane foams are produced by the reaction of polyols with isocyanates in the presence of a blowing agent, with water traditionally used as a blowing agent. The reaction leading to polyurethane foam formation generally consists of the urethane reaction (gelling) and urea reaction (blowing), which is associated with carbon dioxide ($CO_2$) production. Catalysts as well as other auxiliary agents, such as cross-linkers, blowing agents, chain extenders, surfactants, stabilizers, and antioxidants, are typically included in the composition with the polyol and isocyanate components. Catalysts can play a key role in ensuring desirable foam properties by controlling and balancing the gelling and blowing reactions during foam production. Catalysts can also have an effect on moldability and cure speed of the foam.

Tertiary amines and organometallic salts have been used in the art as catalysts for polyurethane foams. However, commonly used tertiary amine catalysts give rise to several problems, particularly in flexible, semi-rigid, and rigid foam applications. Freshly prepared foams using these catalysts often have the typical odor of the amines and give rise to increased fogging due to emission of volatile products.

The presence, or formation, of tertiary amine catalyst vapors in polyurethane products are detrimental to vinyl films or polycarbonate sheets exposed thereto. Specifically, the tertiary amine catalysts present in polyurethane foams have been linked to staining of the vinyl film and degradation of polycarbonate sheets. These PVC staining and polycarbonate decomposition problems are especially prevalent in environments wherein elevated temperatures exist for long periods of time, such as in automobile interiors.

The inventors of the current application have understood that many difficulties exist in producing desirable polyurethane foam products for consumer and industrial applications and that the preparation and identification of amine catalysts desirable for polyurethane foams is still a challenging area. For example, while some catalysts (e.g., see U.S. Pat. No. 4,517,313) are stated to reduce odor and vinyl staining relative to the use of standard triethylenediamine catalysts, they unfortunately provide weaker catalytic activity, and are not up to the standards of conventional catalysts. It is challenging to alter the chemical structure of the amine catalyst without adversely affecting its catalytic activity. In some cases catalysts need to be used at high levels in the polyurethane formulation to compensate for their lack of catalytic activity or mobility during the reactions.

Another issue relates to the stability of compositions, including foam-forming components. Pre-reacted components in a composition may exhibit a tendency to pre-gel or have poor storage stability. Yet another issue is that some catalysts that promote rapid gelling lead to foam processing and foam properties problems. For example, tear strength and elongation at break can be detrimentally affected due to a high level of crosslinking. Further, some catalysts, when subjected to elevated temperatures as are commonly encountered in automobile interiors, migrate within a foam.

The current application provides compounds, compositions, and methods for forming polyurethane foams based on the use of cyclic amine compounds.

SUMMARY

The present invention provides compositions that include cyclic amine compounds, including compositions for the preparation of polyurethane foams using the cyclic amine compounds. The invention also provides methods for preparing cyclic amine compounds of the invention.

The compositions and polyurethane foams are prepared using cyclic amines of Formula I:

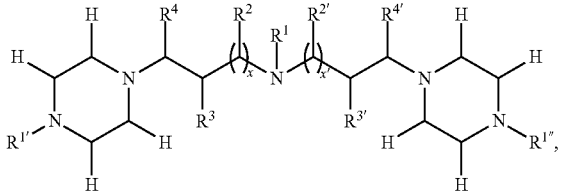

or of Formula II:

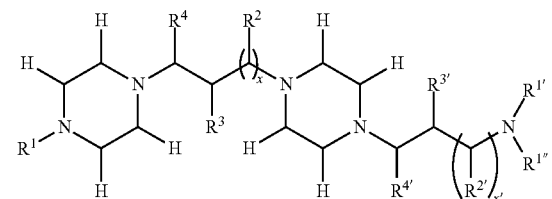

In Formula I or II, $R^1$, $R^{1'}$, and $R^{1''}$ are independently selected from hydrogen and C1-C8 hydrocarbyl groups, wherein at least one of $R^1$, $R^{1'}$, or $R^{1''}$ is a C1-C8 hydrocarbyl group. $R^2$, $R^{2'}$, $R^3$, $R^{3'}$, $R^4$, and $R^{4'}$, independently selected from hydrogen, —$CH_3$, and —$CH_2CH_3$. Also, in Formula I or II, x and x' are independently 0 (a covalent bond) or 1. The cyclic amines of the invention also include acid-blocked derivatives wherein any one or more of the nitrogen(s) in Formula I or II carry a positive charge and are electrostatically blocked by an acid anion.

Exemplary compounds of Formula I or II have x and x' as 0 (a covalent bond); have $R^1$, $R^{1'}$, and $R^{1'''}$ independently selected from —$CH_3$, —$CH_2CH_3$, —$CH_2CH_2CH_3$, —$CH(CH_3)_2$, —$CH_2CH_2CH_2CH_3$, —$CH_2CH(CH_2CH_3)CH_2CH_2CH_3$, and —$CH(CH_3)CH_2CH(CH_3)_2$; and have $R^3$, $R^{3'}$, $R^4$, and $R^{4'}$ as hydrogen. Included as chemical species of the compounds of Formula I and II are N-methyl-2-(4-methylpiperazin-1-yl)-N-(2-(4-methylpiperazin-1-yl)ethyl)ethanamine (methyl-BPEA; meBPEA), N-ethyl-2-(4-ethylpiperazin-1-yl)-N-(2-(4-ethylpiperazin-1-yl)ethyl)ethanamine (ethyl-BPEA; eBPEA), N,N-bis(2-(4-isopropylpiperazin-1-yl)ethyl)propan-2-amine (isopropyl-BPEA; iBPEA), 2-ethyl-N,N-bis(2-(4-(2-ethylhexyl)piperazin-1-yl)ethyl)hexan-1-amine (2-ethylhexyl-BPEA; 2-ehBPEA), N,N-dimethyl-2-(4-(2-(4-methylpiperazin-1-yl)ethyl)piperazin-1-yl)ethanamine, N,N-diethyl-2-(4-(2-(4-ethylpiperazin-1-yl)ethyl)piperazin-1-yl)ethanamine, N-isopropyl-N-(2-(4-(2-(4-isopropylpiperazin-1-yl)ethyl)piperazin-1-yl)ethyl)propan-2-amine, and 2-ethyl-N-(2-ethylhexyl)-N-(2-(4-(2-(4-(2-ethylhexyl)piperazin-1-yl)ethyl)piperazin-1-yl)ethyl)hexan-1-amine.

Acid-blocked cyclic amines of Formula I and II can be formed by protonating any one or more of the nitrogen atom(s) of compounds of Formula I and II, thereby creating quaternary ammonium cation(s), which are electrostatically blocked by the anionic group of an acid(s). In exemplary embodiments, the nitrogens at positions: $R^1$—N, $R^{1'}$—N, or $R^{1'''}$—N carry a positive charge and are electrostatically blocked by an acid anion.

Compounds of Formulas I and II, including acid-blocked species, provide significant advantages in the areas of cyclic amines, including use in compositions containing foam-forming reagents, such as polyurethane foam-forming reagents. Compounds as represented by meBPEA, eBPEA, iBPEA, and 2-eBPEA have desirable physical and catalytic properties for the production of polyurethane foams.

For example, these compounds have one or more of the following properties: (a) liquid at room temperature, (b) a high boiling point (>250° C. at ambient pressure) thereby providing a low volatile organic compound (VOC) profile; (c) desirable viscosity; (d) good color; (e) no undesirable odor; (f) desirable catalytic activity, and (g) stability enhancing properties in the presence of other foam-forming reagents. Use of these compounds can provide distinct benefits for reaction compositions, methods, and polyurethane foams.

With regards to catalytic activity, compounds of Formulas I and II, have structures favorable for the chelatation of water, which in turn promotes higher catalytic (e.g., blowing) activity. Compounds of Formulas I and II (e.g., meBPEA) have structures favorable for chelating water via hydrogen bonding in multiple conformers. In turn, the improved catalytic activity can result in polyurethane foams having more desirable end properties.

The liquid and viscosity properties of the cyclic amine compounds of Formulas I and II can ensure better mixing in the foam-forming compositions. The cyclic amine compounds of Formula I and II are also easier to handle as compared to more volatile amines or amines that are in solid form, or amine adduct epoxies (reactions of amines with an epoxy) which can be viscous. Due to both the exothermic nature of the foam-forming reactions and the elevated temperatures for reaction, many known amine catalysts which are volatile cause an odorous release which can be undesirable. Further, the desirable viscosity of cyclic amine compounds of the invention allows for better molecular mobility which can lead to a more thorough distribution of the compound with enhanced foam-forming reactions, which ultimately provides foams with improved properties.

It has also been found that cyclic amine compounds of Formula I or II can be used to enhance the stability of compositions that include blowing agents, such as hydrofluorochloro-carbons or hydrofluorocarbons. Blowing agents play a role in generating the cellular structure via a foaming process and are typically used when the foam-forming materials are in a liquid state. Hydrofluorochlorocarbon or hydrofluorocarbon blowing agents trapped in the cells of the foams can reduce foam density and provide improved thermal and acoustic insulation. It has been found that as compared to some traditional amine blowing catalysts, the cyclic amine compounds of Formula I or II enhance the stability of compositions (e.g., such as by preventing clouding of the composition due to incompatibility) that include a hydrofluorochlorocarbon or hydrofluorocarbon blowing agent, such as 1-chloro-3,3,3 trifluoropropene.

As another benefit, the cyclic amines of Formula I or II have good color and no undesirable odor. These desirable properties can carry over into products made from the cyclic amines such as polyurethane foams. For example, a polyurethane foam with a good color may be colorless, or substantially colorless, and may be used to make articles that are resistant to staining, etc., which in turn have a higher consumer value. Polyurethane foam products that do not have any objectionable odor also have a higher consumer value.

In one aspect, the invention provides a composition comprising (a) a cyclic amine of Formula I or II, or an acid-blocked derivative thereof, (b) a polyol, and (c) a polyisocyanate.

In another aspect, the invention provides a composition comprising (a) a cyclic amine of Formula I or II, or an acid-blocked derivative thereof, and (b) a hydrofluorochlorocarbon or hydrofluorocarbon. This composition can further include polyurethane foam-forming components, such as a polyol and a polyisocyanate.

The invention also provides polyurethane foams made using a cyclic amine of Formula I or II, or an acid-blocked derivative thereof. Foams made using a cyclic amine of Formula I or II, or an acid-blocked derivative thereof, can include a blowing agent such as a hydrofluorochlorocarbon or hydrofluorocarbon, which can provide the foam with one or more desired properties, such as an insulating property.

Polyurethane foams, including those that are flexible or rigid, formed using a cyclic amine compound of Formula I or II, or an acid-blocked derivative thereof, can be used for a variety of applications. Such applications include use in commercial and domestic furniture and bedding; commercial and personal vehicles, such as in seating and interior panels; refrigerators and freezers; construction materials, garments, clothing, and footwear; packaging materials; as well as electronics and industrial machinery, among others.

The invention also provides a method for preparing a compound of Formula I or II. The method comprises a step of reacting a compound of Formula III:

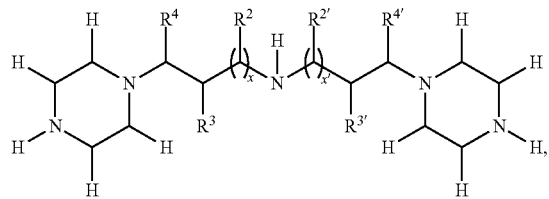

or a compound of Formula IV:

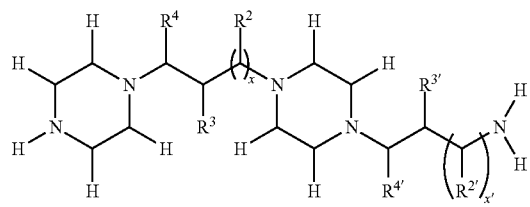

with a C1-C8 aldehyde or C3-C8 ketone in the presence of a reducing agent. In Formula III or IV, $R^2$, $R^{2'}$, $R^3$, $R^{3'}$, $R^4$, and $R^{4'}$ are independently selected from hydrogen, —$CH_3$, and —$CH_2CH_3$; and x and x' are independently 0 (a covalent bond) or 1.

DETAILED DESCRIPTION

Reference will now be made in detail to representative embodiments of the invention. While the invention will be described in conjunction with the enumerated embodiments, it will be understood that they are not intended to limit the invention to those embodiments. On the contrary, the invention is intended to cover all alternatives, modifications, and equivalents that may be included within the scope of the present invention as defined by the claims.

One skilled in the art will recognize many methods and materials similar or equivalent to those described herein, which could be used in and are within the scope of the practice of the present invention. The present invention is in no way limited to the methods, materials, and compositions described.

Unless defined otherwise herein, technical and scientific terms used herein have the same meaning as commonly understood by one of ordinary skill in the art to which this invention belongs. Although any methods, devices, and materials similar or equivalent to those described herein can be used in the practice or testing of the invention, the preferred methods, devices and materials are now described.

Compounds of Formulas I and II can be formed by the reductive alkylation of a compound such as bis(2-(piperazin-1-yl)ethyl)amine (BPEA). The preparation of BPEA and other cyclic amines having a bis-piperazinyl-amine structure is described in commonly assigned International Patent Application No.: PCT/US2012/064971 entitled Formation of Higher Molecular Weight Cyclic Polyamine Compounds from Cyclic Polyamine Compounds, Published as WO2013/101345 on Jul. 4, 2013 (King).

A compound of Formula I or II can be prepared by the reductive alkylation of a compound of Formula III or IV, as shown below. In Formula III:

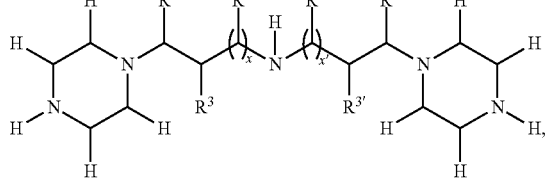

or in Formula IV:

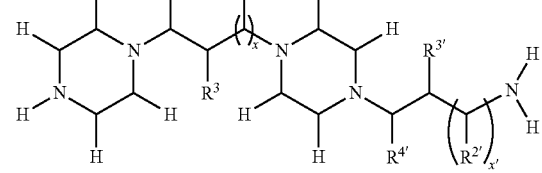

$R^2$, $R^{2'}$, $R^3$, $R^{3'}$, $R^4$, and $R^{4'}$, independently selected from hydrogen, —$CH_3$, and —$CH_2CH_3$; and x and x' are independently 0 (a covalent bond) or 1.

Examples of cyclic amines of Formula III that can be reductively alkylated include bis(2-(piperazin-1-yl)ethyl)amine (BPEA), bis(3-(piperazin-1-yl)propyl)amine, bis(1-(piperazin-1-yl)propan-2-yl)amine, and bis(2-(piperazin-1-yl)propyl)amine.

Examples of cyclic amines of Formula IV that can be reductively alkylated include 2-(4-(2-(piperazin-1-yl)ethyl)piperazin-1-yl)ethanamine, 3-(4-(3-(piperazin-1-yl)propyl)piperazin-1-yl)propan-1-amine, 1-(4-(1-(piperazin-1-yl)propan-2-yl)piperazin-1-yl)propan-2-amine, and 2-(4-(2-(piperazin-1-yl)propyl)piperazin-1-yl)propan-1-amine.

Reductive alkylation is an effective method to synthesize secondary and tertiary amines from primary and secondary amines using aldehydes and ketones. Reductive alkylation can be carried out by reacting a compound of Formula III or IV with a C1-C8 aldehyde or a C3-C8 ketone in the presence of a reducing agent. Exemplary aldehydes include formaldehyde, acetaldehyde, propionaldehyde, butyraldehyde, and 2-ethylhexanal. Exemplary ketones include acetone, 2-butanone, 3-pentanone, and methyl isobutyl ketone. The reaction can be carried out with a desired amount of a compound of Formula III or IV and an aldehyde or a ketone to provide a partially or fully alkylated product (Formula I or II). Partial alkylation can be carried out using less than the molar equivalents of the ketone or aldehyde relative to the molar equivalents of nitrogen on a compound of Formula III or IV (e.g., 2 molar equivalents, or 1 molar equivalent for 3 NH functionalities). Full alkylation can be carried out using an equimolar number of equivalents, or greater, of the ketone or aldehyde relative to the equivalents of NH functionality. Reductive alkylation can be carried out in the presence of hydrogen and a hydrogenation catalyst, such as a nickel-based catalyst, at elevated temperatures, and in a suitable solvent, such as methanol.

Partial or full reductive alkylation can provide a cyclic amine compound of Formula I:

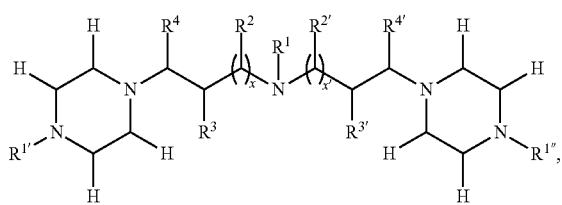

or of Formula II:

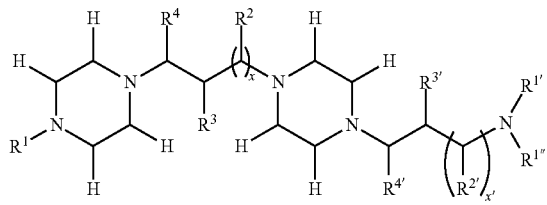

In Formula I or II, $R^1$, $R^{1'}$, and $R^{1'''}$ are independently selected from hydrogen and C1-C8 hydrocarbyl groups, wherein at least one of $R^1$, $R^{1'}$, or $R^{1'''}$ is a C1-C8 hydrocarbyl group. $R^2$, $R^{2'}$, $R^3$, $R^{3'}$, $R^4$, and $R^{4'}$ are independently selected from hydrogen, —$CH_3$, and —$CH_2CH_3$. Also in Formula I or II x and x' are independently 0 (a covalent bond) or 1.

Hydrocarbyl groups as referred to herein are substituted or unsubstituted, linear, branched, or cyclic hydrocarbyl groups, such as alkyl, aryl, aralkyl, or the like.

More specifically, in some cases, in Formula I or II, at least one of $R^1$, $R^{1'}$, or $R^{1'''}$ is a C1-C3 hydrocarbyl group. For example, if one or two of $R^1$, $R^{1'}$, and/or $R^{1'''}$ is/are a C1-C3 hydrocarbyl group(s), the non-C1-C3 hydrocarbyl group(s) of $R^1$, $R^{1'}$, and/or $R^{1'''}$ can be hydrogen. In this case the compound of Formula I or II can be partially alkylated. In other cases in Formula I or II, all $R^1$, $R^{1'}$, and groups are independently selected from C1-C3 hydrocarbyl groups, which can be the same of different. In this case the compound of Formula I or II can be fully alkylated.

In some cases of full alkylation, all of $R^1$, $R^{1'}$, and $R^{1'''}$ are independently selected from —$CH_3$, —$CH_2CH_3$, —$CH_2CH_2CH_3$, —$CH(CH_3)_2$, —$CH_2CH_2CH_2CH_3$, —$CH_2CH(CH_2CH_3)CH_2CH_2CH_3$, and —$CH(CH_3)CH_2CH(CH_3)_2$. In more specific cases of full alkylation, all of $R^1$, $R^{1'}$, and $R^{1'''}$ are —$CH_3$.

Included as chemical species in the compounds of Formula I and II are N-methyl-2-(4-methylpiperazin-1-yl)-N-(2-(4-methylpiperazin-1-yl)ethyl)ethanamine (methyl-BPEA; meBPEA), N-ethyl-2-(4-ethylpiperazin-1-yl)-N-(2-(4-ethylpiperazin-1-yl)ethyl)ethanamine (ethyl-BPEA; eBPEA), N,N-bis(2-(4-isopropylpiperazin-1-yl)ethyl)propan-2-amine (isopropyl-BPEA; iBPEA), and 2-ethyl-N,N-bis(2-(4-(2-ethylhexyl)piperazin-1-yl)ethyl)hexan-1-amine (2-ethylhexyl-BPEA; 2-eBPEA), N,N-dimethyl-2-(4-(2-(4-methylpiperazin-1-yl)ethyl)piperazin-1-yl)ethanamine, N,N-diethyl-2-(4-(2-(4-ethylpiperazin-1-yl)ethyl)piperazin-1-yl)ethanamine, N-isopropyl-N-(2-(4-(2-(4-isopropylpiperazin-1-yl)ethyl)piperazin-1-yl)ethyl)propan-2-amine, and 2-ethyl-N-(2-ethylhexyl)-N-(2-(4-(2-(4-(2-ethylhexyl)piperazin-1-yl)ethyl)piperazin-1-yl)ethyl)hexan-1-amine.

In some embodiments, the invention provides cyclic amine derivatives of Formula I or II where any one or more of the nitrogen(s) in the cyclic amine derivative carry a positive charge and are electrostatically blocked by an acid anion. Such acid blocked cyclic amine derivatives can be formed by protonating any one or more of the nitrogen atom(s) of compounds of Formula I and II, thereby creating quaternary ammonium cation(s), which are electrostatically blocked by the anionic group of an acid(s). As used herein, a "derivative" refers to an acid-blocked species of Formula I and II.

An exemplary process for acid blocking involves mixing a non-acid blocked compound of Formula I or II with a desired acid, or combination of acids, in solution. Solvents that can be used include water, ethylene glycol, diethylene glycol, dipropylene glycol, or butanediol, or mixtures thereof. An exemplary catalyst amount is at weight ratio in the range of 10-80% in the solvent. The non-acid blocked compound of Formula I or II is mixed with the acid to provide a pH value of 7.0 or higher in an aqueous solution. Techniques for acid blocking using a dicarboxylic acid are described in EP0989146 (Kometani, et. al).

Exemplary acid blocking compounds include anions of saturated dicarboxylic acids such as succinic acid, glutaric acid, adipic acid, pimelic acid, suberic acid, azelaic acid, sebacic acid, undecanedioic acid, decane-dicarboxylic acid, 1,11-undecane-dicarboxylic acid, 1,12-dodecane-dicarboxylic acid, and hexadecanedioic acid.

Exemplary acid blocking compounds also include anions of saturated monocarboxylic acids such as acetic acid, propionic acid, butyric acid, valeric acid, caproic acid, caprylic acid, caproic acid, 2-ethylhexanoic acid, and 2-cyanoacetic acid. Exemplary acid blocking compounds can also be obtained from the ring opening of fatty acid anhydrides.

The extent of acid blocking can be determined from factors such as the chemical structure of a compound of Formula I or II, and the amount and type of acid reagent used for blocking. The acid blocked cyclic amine derivatives can include partially blocked cyclic amine derivatives and fully blocked cyclic amine derivatives. A monoacid which has one anionic group will be able to block one cationic group of a protonated amine, whereas a diacid having two anionic groups will be able to block two cationic group(s), such as on the same or on different cyclic amine compounds. Exemplary acid blocked cyclic amine derivatives showing acid blockage at the protonated amines of $R^1$—N, $R^{1'}$—N, or $R^{1'''}$—N include those of Formula V:

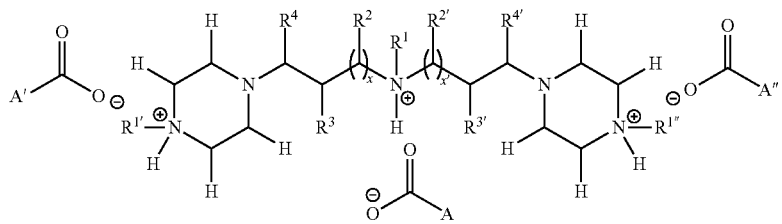

In formula V, $R^1$, $R^{1'}$, and $R^{1''}$ are independently selected from hydrogen and C2-C8 hydrocarbyl groups. Optionally, at least one or more of $R^1$, $R^{1'}$, and $R^{1''}$ is a C1-C8 hydrocarbyl group. In Formula V, $R^2$, $R^{2'}$, $R^3$, $R^{3'}$, $R^4$, and $R^{4'}$ are independently selected from hydrogen, —CH$_3$, and —CH$_2$CH$_3$. Also in Formula V x and x' are independently 0 (a covalent bond) or 1. A, A', and A" are independently selected from —$R^5R^6$, where $R^5$ is a linear, branched, or cyclic C2-C14 hydrocarbylene group, and R6 is —H or —C(O)O$^-$. For full blocking of the protonated amines as illustrated, Formula V shows a 1:3 molar ratio of cyclic amine to acid, when the acid blocking compound is a monocarboxylic acid. However, if the acid blocking compound is a dicarboxylic acid, the molar ratio of cyclic amine to acid is 2:3 for full blocking (the other cyclic amine is not shown).

Prior to inclusion in a composition, such as a polyurethane foam-forming composition, the compound of Formula I or II can be separated (refined) by any method known in the art. Methods for purification or separation include conventional distillation technology using dividing wall columns, membrane separation, melt crystallization, and reactive distillation.

Compounds of Formula I or II can be used in "neat" form, as, for example, a liquid, with no solvent present. For example, N-methyl-2-(4-methylpiperazin-1-yl)-N-(2-(4-methylpiperazin-1-yl)ethyl)ethanamine (methyl-BPEA; meBPEA) is a liquid at room temperature (~25° C.), and has a boiling point (760 torr) of ~338° C. Alternatively, the compounds of Formula I or II can be used along with a solvent, or combination of solvents. Desirably, the solvent is not unduly reactive with the cyclic amine product of Formula I or II. Some examples of solvents that could be in mixture with the cyclic amine include saturated hydrocarbons such as pentane, hexane, octane, nonane, decane, or the like; aromatic hydrocarbons such as toluene, benzene, xylene, ether, combinations of these, and the like.

Cyclic amine compounds of Formula I or II can also be described in terms of the molecular weight. Exemplary cyclic amine compounds of Formula I or II have a molecular weight in the range of about 255 Da to about 690 Da, about 269 Da to about 600 Da, or about 283 Da to about 578 Da.

A compound of Formula I or II, an acid blocked cyclic amine derivative thereof, or a mixture of compounds of Formula I or II or acid blocked derivatives thereof, can be present in a composition with components used for making foams. For example, other aspects of the invention are directed to compositions for making polyurethane foams, methods for making polyurethane foams, and polyurethane foams made using a cyclic amine of Formula I or II, or an acid blocked derivative thereof. In some modes of practice, a cyclic amine compound of Formula I or II or an acid blocked derivative thereof can be used in a composition to provide catalytic activity during the foam forming reaction. Included in the composition along with (a) the cyclic amine or acid-blocked derivative are (b) a polyol compound, and (c) a polyisocyanate.

Cyclic amine compounds of Formula I or II, or acid blocked derivates thereof, can be used in a composition at a desired concentration to provide catalytic activity during the foam forming reaction. Exemplary concentrations of the cyclic amine compound of Formula I or II, or acid blocked derivate thereof, may be different for flexible or rigid foams. For flexible foams, exemplary concentrations of the cyclic amine or derivative thereof are in the range of about 0.02 wt. % to about 1.5 wt. %, 0.05 wt. % to about 1 wt. %, or 0.1 wt. % to about 0.8 wt. % by weight of the polyol. For rigid foams, exemplary concentrations of the cyclic amine or derivative are in the range of about 0.1 wt. % to about 3 wt. %, 0.2 wt. % to about 2 wt. %, or 0.5 wt. % to about 1.5 wt. % by weight of the polyol.

One or more catalysts that are different than the cyclic amine of Formula I or II, or acid blocked derivate thereof, may optionally be used in the composition along with the cyclic amine or derivative. Exemplary gelling catalysts that can optionally be used in combination with the cyclic amine or derivative thereof include, but are not limited to, N,N-bis(3-dimethylamino-propyl)N-isopropanol-amine; N,N-di-methylaminoethyl-N'-methyl ethanolamine; N,N,N'-trim-ethylaminopropyl ethanolamine; N,N-dimethylethanolamine; N,N-dimethyl-N',N'-2-hydroxy (propyl)-1,3-propylenediamine; dimethylaminopropylamine; (N,N-dimethylaminoethoxy) ethanol; methylhydroxyethylpiperazine, bis(N,N-dimethyl-3-aminopropyl)amine; N,N-dimethyl-aminopropyl urea; N,N'-bis(3-dimethylaminopropyl); bis(dimethylamino)-2-propanol; N-(3-aminopropyl)imidazole; N-(2-hydroxypro-pyl)imidazole; and N-(2-hydroxyethyl) imidazole. The type and amount of optional gelling catalyst can be chosen based on the factors such as the components in the foam-forming composition and desired properties of the formed foam.

Exemplary blowing catalysts that can optionally be used in combination with the cyclic amine or derivative thereof include non-fugitive blowing catalysts include, but are not limited to, 2[N-(dimethylaminoethoxy-ethyl)-N-methyl-amino]ethanol; dimethylaminoethoxy-ethanol; N,N,N'-trim-ethyl-N'-3-amino-propyl-bis(aminoethyl) ether; and N,N,N'-trimethyl-N'-aminopropyl-bis(aminoethyl)ether. The type and amount of optional blowing catalyst can be chosen based on the factors such as the components in the foam-forming composition and desired properties of the formed foam.

Exemplary polyols that can be used to produce polyurethane materials with the cyclic amine catalysts of Formula I or II, include those that are well known in the art. These include polyols described herein, commercially available polyol, and polyols described in the literature. General classes of polyols that can be used in the polyurethane foam forming composition include polyether polyols, polyester polyols, polyhydroxy-terminated acetal resins, hydroxyl-terminated amines, and polyamines (see, for example, U.S. Pat. No. 4,394,491). Other polyols classes include polyalky-lene carbonate-based polyols and polyphosphate-based polyols. Copolymer polyols, some of which can be prepared by grafting methodologies, include styrene/acrylonitrile (SAN) copolymer polyols, polyisocyanate poly addition (PIPA) polyols, and polyharnstoff dispersion (PHD) copo-lymer polyols. Copolymer polyols can include polymer segments other than the polyol portion to introduce desirable properties into the copolymer polyol, such as hardness. Exemplary polyols are also described in the Polyurethane Handbook (G. Oertel, Hanser publishers). The polyurethane foam forming composition can optionally include mixtures of one or more different polyol types, such as mixtures of two different polyols selected from polyol homopolymers and polyol copolymers.

Exemplary polyols that can be used in the foam-forming composition include alkylene oxide-based polyols prepared from polyol-generating monomers such as ethylene oxide, propylene oxide, butylene oxide, or combinations thereof. Alkylene oxide-based polyols can be made from monomer initiators with active hydrogen atoms, such as those having two or more hydroxyl or amine groups. In some polyol preparations, monomer initiators have from 2 to 8, or more specifically 2 to 6 active hydrogen atoms. Exemplary monomer initiators include organic dicarboxylic acids, such as succinic acid, adipic acid, phthalic acid and terephthalic acid and polyhydric alcohols, in particular dihydric to octahydric alcohols or dialkylene glycols, for example, ethanediol, 1,2- and 1,3-propanediol, diethylene glycol, dipropylene glycol, 1,4-butanediol, 1,6-hexanediol, glycerol, trimethylolpropane, pentaerythritol, sorbitol, and sucrose, or blends thereof. Other initiators include linear and cyclic compounds containing an amine such as N-methyldiethanolamine, triethanolamine, and various isomers of toluene diamine.

The particular polyol or polyol mixture, and polyol amount used in the polyurethane foam forming composition can be chosen based on the factors such as the desired polyurethane foam properties and/or the particular end use of the foam product. Properties of the polyol such as molecular weight or hydroxyl number can be chosen to provide foam characteristics selected from: low density, high density, conventional, high resilient, hot molding, cold molding, flexible, and rigid, and desired combinations thereof. For many applications or foam properties, the hydroxyl number of the polyol is in the range of about 15 to about 800, with a preferred hydroxyl number for flexible foams in the range of about 20 to about 60, and a preferred hydroxyl number for flexible foams in the range of about 200 to about 800.

Compositions for the production of flexible polyurethane foams typically include a polyether polyol and/or a polyester polyol. The polyol generally has an average functionality ranging from 2 to 5, preferably 2 to 4, and an average hydroxyl number ranging from 20 to 100 mg KOH/g, preferably from 20 to 70 mg KOH/g (see, for example, U.S. Pat. No. 7,361,695).

For flexible foams, the hydroxyl number of the base polyol can be in the range of about 20 to about 60 with ethylene oxide (EO) capping, and for slabstock foams the hydroxyl number can be in the range of about 25 to about 75 (see, for example, U.S. Pat. No. 7,361,695).

Polyurethane foam-forming compositions also include a polyisocyanate, such as a polyisocyanate selected from aliphatic, cycloaliphatic, arylaliphatic, and aromatic polyisocyanates. Aromatic polyisocyanates are preferred for the production of flexible foams.

Exemplary polyisocyanates include the 4,4'-, 2,4' and 2,2'-isomers of diphenylmethane diisocyante (MDI), blends thereof; polymeric and monomeric MDI blends; toluene-2,4- and 2,6-diisocyanates (TDI), blends thereof; biuret modified TDIs, TDI/MDI blends; polymerized isocyanates, m- and p-phenylenediisocyanate, chlorophenylene-2,4-diisocyanate, diphenylene-4,4'-diisocyanate, 4,4'-diisocyanate-3,3'-dimethyldiphenyl, 3-methyldiphenyl-methane-4,4'-diisocyanate, diphenyletherdiisocyanate, 2,4,6-triisocyanatotoluene, and 2,4,4'-triisocyanatodiphenylether (see, for example, U.S. Pat. No. 7,361,695).

Examples of aliphatic polyisocyanates include ethylene diisocyanate, 1,6-hexamethylene diisocyanate, isophorone diisocyanate, cyclohexane 1,4-diisocyanate, 4,4'-dicyclohexylmethane diisocyanate, saturated analogues of the above mentioned aromatic isocyanates, and mixtures thereof.

Isocyanate-terminated prepolymers are prepared by reacting an excess of polyisocyanate with polyols, including aminated polyols or imines/enamines thereof, or polyamines (see, for example, U.S. Pat. No. 7,361,695).

For some foam products such as flexible polyurethane foams, water can optionally be used as a blowing agent. Exemplary amounts of water are in the range of about 0.5 to about 10 parts by weight, or more specifically in the range of about 1 to about 6 parts by weight based on 100 parts by weight of the polyol. Carboxylic acids or salts can also optionally be used as blowing agents.

Use of carbon dioxide, either as a gas or as a liquid, as auxiliary blowing agent, in addition to water can optionally be used. During foam formation, atmospheric pressure can be adjusted, frothing can be used, or combinations thereof, as described in U.S. Pat. No. 5,194,453 to vary foam density.

For the preparation of some thermally insulating polymeric foams, a low-conductivity gas such as a hydrochlorofluorocarbon (HCFC) or a hydrofluorocarbon (HFC) can be used as a blowing agent. Polyurethane insulating foams can be prepared using HCFCs or HFCs to provide polyurethane closed-cell foam insulation materials. The high thermal resistance of the HCFCs or HFCs can provide polyurethane insulation with R-values generally in the range of about R-6 to about R-8 per inch. R-values are a measure of thermal resistance being a ratio of the temperature difference across an insulator and the heat flux (heat transfer per unit area) through it.

A "hydrochlorofluorocarbon" (HCFC) refers to a compound having carbon, hydrogen, chlorine, and fluorine atoms; a "hydrofluorocarbon" (HFC) refers to a carbon compound having carbon, hydrogen, and fluorine groups. Typical HCFCs and HFCs are derived from methane, ethane, propane, and butane. Exemplary hydrofluorochlorocarbons and hydrofluorocarbons are selected from the group consisting of chlorodifluoromethane; 1-chloro-1,1-difluoroethane; 1,1-difluoroethane; 1,2-difluoroethane; 1,1,1,2-tetrafluoroethane; 2,2-dichloro-1,1,1-trifluoroethane; 1,2,2-trifluoroethane; 1,1,1,2,3,3,3-heptafluoropropane; 1,1,1,3,3-pentafluoropropane; 1,2-dichloro-3,3,3-trifluoropropene; 1-chloro-1,3,3,3-tetrafluoropropane; 1-chloro-3,3,3 trifluoropropene; cis-1,3,3,3-tetrafluoropropene; 1,2,2,3,3-pentafluoropropane; 1,1,1,3,3-pentafluorobutane; and 1,1,2,2-tetrafluoroethyl methyl ether.

In some preparations, the amount of the HCFC and HFC blowing agent is in the range of about 1 to about 40 parts by weight, about 4 to about 35 parts by weight, or more specifically about 6 to about 30 parts by weight based on 100 parts by weight of the polyol. Mixtures of blowing agents can also be used. For example, the blowing agent can comprise a mixture of two or more HCFC and/or HFC blowing agents, or the mixture can comprise a mixture of one or more HCFC or HFC blowing agents and a non-halogenated hydrocarbon blowing agent such butane, pentane, or cyclopentane.

Other components can be used in addition to the cyclic amine of Formula I or II, or acid blocked derivative thereof and the foam-forming reagents (polyol and polyisocyanate components). These other components include, but are not limited to surfactants, preservatives, flame retardants, colorants, antioxidants, reinforcing agents, stabilizers, and fillers.

In making polyurethane foam, it is generally preferred to employ an amount of a surfactant to stabilize the foaming reaction mixture until it cures. In some formulations, the composition includes a liquid or solid organosilicone surfactant. Other surfactants include polyethylene glycol ethers of long-chain alcohols, tertiary amine or alkanolamine salts of long-chain alkyl acid sulfate esters, alkyl sulfonic esters, and alkyl arylsulfonic acids. Surfactants can be used in amounts sufficient to stabilize the foaming reaction mixture against collapse and the formation of a desired cell structure. Exemplary amounts of surfactant are in the range of about 0.2 to about 3 parts of the surfactant per 100 parts by weight total polyol. Mixtures of surfactants can be used.

In some formulations, the composition can include an organometallic catalyst to promote the reaction of the polyol with the polyisocyanate. Exemplary organometallic catalysts include organomercury, organolead, organoferric and organotin catalysts. Exemplary tin catalysts include stannous chloride, tin salts of carboxylic acids such as dibutyltin di-laurate, as well as other organometallic compounds such as disclosed in U.S. Pat. No. 2,846,408. A catalyst for the trimerization of polyisocyanates, resulting in a polyisocyanurate, such as an alkali metal alkoxide may also optionally be used in the foam forming compositions. Exemplary amounts of optional organometallic catalysts range from about 0.001 to about 1 percent in the composition.

Other components that can optionally be added to the foam forming composition include crosslinking agents and chain extenders. Exemplary crosslinking agents and chain extenders include low-molecular polyhydric alcohols such as ethylene glycol, diethylene glycol, 1,4-butanediol, and glycerin; low-molecular weight amine polyols such as diethanolamine and triethanolamine; diamines such as ethylenediamine, xylenediamine; and methylene-bis(o-chloroaniline). The use of such crosslinking agents or chain extenders is known in the art as disclosed in U.S. Pat. Nos. 4,863,979 and 4,963,399, and EP 549,120.

In some modes of practice, a polyurethane foam forming composition including (a) a compound of Formula I or II, or an acid-blocked derivative thereof; (b) a HCFC or HFC; (c) a polyol; and (d) a polyisocyanate is used for a sprayed or foamed-in-place application. Low-density foams formed using a composition including these components can be sprayed into a desired area and rapidly expanded to seal and fill the cavity. Exemplary uses of sprayed or foamed-in-place compositions include residential and commercial building insulation.

Foams produced using a compound of Formula I or II, or an acid-blocked derivative thereof, can be used in applications known in the industry. For example, flexible foams find use in applications such as vehicle parts, such as seats, armrests, dashboards or instrument panels, sun visors, door linings, noise insulation parts either under the carpet or in other parts of the car interior or in the engine compartment, as well as in many domestic applications such as shoe soles, cloth interliners, appliance, furniture and bedding.

Processes for producing polyurethane products are well known in the art. In general components of the polyurethane-forming reaction mixture can be mixed together in any convenient manner, for example by using any of the mixing equipment described in the prior art for the purpose such as described in Polyurethane Handbook, by G. Oertel, Hanser publisher.

The polyurethane products are either produced continuously or discontinuously, by injection, pouring, spraying, casting, calendering, etc. The foams can be made under free rise or molded conditions, at atmospheric pressure, reduced or increased air pressure, with or without release agents, in-mold coating, or any inserts or skin put in the mold. Flexible molded foams can be mono- or dual-hardness.

The polyurethane foams can optionally be described by one or more foam properties, including, but not limited to: airflow, density, indentation force deflection (IFD), sag factor, recovery ratio, guide factor, compression load deflection (CLD), percent (%) compression set, tensile strength, elongation, tear, permeability, impact resilience, and thickness.

Density is weight per unit volume (weight/volume) and typically expressed as lbs/ft3 (pcf) or g/L. Exemplary foam densities are in the range of about 0.4 lbs/ft$^3$ to about 50 lbs/ft$^3$, about 0.5 lbs/ft$^3$ to about 30 lbs/ft$^3$, about 1 lbs/ft$^3$ to about 10 lbs/ft$^3$, about 1.5 lbs/ft$^3$ to about 5 lbs/ft$^3$, or more specifically in the range of about 1.75 lbs/ft$^3$ to about 3 lbs/ft$^3$.

Compression force deflection (CFD), such as measured by the ISO 3386/1 standard, is a testing standard designed to measure the compression stress/strain (load divided by specimen surface area at a certain compression percentage) characteristic of foam. CFD is also a measure of firmness and is expressed in kilopascals (kPa) or pounds per square inch (psi), at a given percentage deflection. Foam compositions can be prepared to provide foam with a desired CFD, or a CFD within a desired range.

Percent compression set (CS), such as measured by the ISO 1856 standard, is a measure of the permanent deformation of foam after it has been compressed between two metal plates for a controlled time period and temperature condition. The standard conditions are 22 hours at 70° C. (158° F.). Exemplary compression set values are less than 20%, less than 10%, or more specifically less than 5%.

Tensile strength is a measure of the amount of force required to break an area of foam as it is pulled apart, and is generally expressed in pounds per square inch (psi). Exemplary tensile strength values are greater than about 10 psi or more specifically greater than about 14 psi.

Impact Resilience (Ball Rebound), such as measured by the ASTM D-3574-H standard, is a measure of elasticity, bounce, or springiness of foam and is expressed as a % of return, or % resilience. Foam compositions can be prepared to provide a foam with a desired resilience, or a resilience within a desired range.

EXAMPLE 1 meBPEA Preparation 27.3 grams (0.11 mol) of bis(2-(piperazin-1-yl)ethyl) amine (BPEA) dissolved in 80 mL of methanol was charged to a 300 mL 3-neck flask. With stirring under nitrogen, 23.7 grams (0.43 mol) of methyl formal (55% formaldehyde) was added slowly with cooling to the flask while maintaining a temperature of <40° C. to give a light yellow colored solution. The material was diluted with an additional 100 mL of methanol and charged to a pressure reactor which contained 10.1 grams of Raney® Ni grade R3111 (Grace Davison) catalyst which had been washed three times with methanol. The reactor was purged and evacuated three times with nitrogen, followed by three times with hydrogen. Hydrogen was added to the reactor at room temperature to an initial pressure of ca. 500 psig. For one hour additional hydrogen was added to maintain a reactor pressure of 360-580 psig. The reactor was then heated to 70° C. and held at that temperature for ca. 2.5 hours. The reactor was cooled, the contents filtered via vacuum and the filtrate concentrated on a rotovap to give 31 grams (100%) of N-methyl-2-(4-methylpiperazin-1-yl)-N-(2-(4-methylpiperazin-1-yl)ethyl) ethanamine (methylated BPEA) as a yellow oil.

EXAMPLES 2-4

Polyurethane Foam Preparation

Foams of Examples 2-4 were made in the laboratory on the bench by pre-blending polyols, surfactant, catalysts, and water of the types and amounts according to Table 1. The pre-blends were conditioned at 25° C. Isocyanate, also conditioned at 25° C., was added to the pre-blends under stirring at 2800 RPM for 5 seconds. At the end of mixing the reactants were poured into a 30×30×10 cm aluminum mold heated at 50° C. which was subsequently closed. Prior to use, the mold was sprayed with a release agent. After 6 minutes the cured foam part was manually demolded and allowed to sit for 7 days at 23° C. in 50% relative humidity. Afterwards, testing of the foam properties was conducted. Various foam properties were tested and are shown in Table 2.

TABLE 1

|  | Example 2 | Example 3 | Example 4 |
|---|---|---|---|
| Polyol A | 100 | 100 | 100 |
| Polyol B | 3 | 3 | 3 |
| H2O | 3.8 | 3.8 | 3.8 |
| Surfactant | 1.35 | 1.35 | 1.35 |
| Catalyst A | 0.196 | — | 0.196 |
| Catalyst B | 0.075 | 0.075 | — |
| Catalyst C | — | 0.165 | 0.109 |
| Index | 100 | 100 | 100 |
| Polyisocyanate | 62.2 | 62.2 | 62.2 |

| Component | Tradename | Description |
|---|---|---|
| Polyol A | VORANOL ™ CP 6001 | An ethylene oxide capped polyol with a functionality of 3 and an OH number of 27.5. |
| Polyol B | VORANOL ™ CP 1421 | A polyether polyol with a functionality of 3 and an OH number of 33.5. with HEW of 1675 gm/mole (Dow). |
| Surfactant | Tegostab B4113 | A surfactant for HR MDI foams (Evonik). |
| Catalyst A | Dabco 33LV | A blowing catalyst containing 33% triethylene diamine and 67% dipropylene glycol (Air Products). |
| Catalyst B | Niax A1 | A blowing catalyst containing 70 percent bis(2-dimethylaminoethyl) ether, diluted with 30 weight percent of dipropylene glycol (Momentive). |
| Catalyst C |  | mBPEA |
| Polyisocyanate | PAPI ™ 94 | Polymeric MDI with a NCO level of 31.9% and a functionality of 2.3 (Dow). |

TABLE 2

|  | LIMS Ref | Example 2 | Example 3 | Example 4 |  |
|---|---|---|---|---|---|
| Airflow-dm$^3$/s | Mean | 3.03 | 3.348 | 3.383 | cu_ft/min |
|  | Std. Dev | 0.04 | 0.02 | 0.12 |  |
|  | % COV | 1.20% | 0.63% | 3.45% | % |
| CFD ISO-3386 | 25% CFD 1 | 7.35 | 7.22 | 6.62 | kPa |
|  | 40% CFD 1 | 9.68 | 9.59 | 9.31 | kPa |
|  | 65% CFD 1 | 25.55 | 26.56 | 25.1 | kPa |
|  | Hysteresis % 1 | 41.46% | 44.72% | 41.83% | % |
| CS 75% ISO, Original, Parallel | CT | 9.17% | 9.57% | 8.19% | % |
|  | Std Dev of CT | 0.2752 | 0.1954 | 0.2152 |  |
|  | % COV of CT | 3.00% | 2.04% | 2.63% | % |
| Density: ASTM | Mean Density | 2.614 | 2.685 | 2.607 | lbm/cu_ft |
|  | Std Dev of Density | 0.02 | 0 | 0.01 |  |
|  | % COV of Density | 0.83% | 0.04% | 0.28% | % |
| RESIL_TEST: ASTM D-3574- H Ball Rebound | Average Resiliency | 46.40% | 45.40% | 43.40% | % |
|  | Std. Dev | 1.34 | 0.89 | 0.55 |  |
|  | % COV | 2.89% | 1.96% | 1.27% | % |
| Tensile: (D3574) | Tensile strength mean | 15.255 | 17.077 | 16.96 | psi |
|  | Tensile Strength (Std. Dev.) | 2.32 | 0.401 | 0.86 |  |
|  | Tensile Strength COV, % | 15.21% | 2.35% | 5.07% | % |
|  | Elongation at break (mean), % | 52.72% | 61.44% | 55.12% | % |
|  | Elongation at break (Std Dev) | 9.702 | 5.547 | 4.348 |  |
|  | % Elongation @Break (% COV) | 18.40% | 9.03% | 7.89% | % |

EXAMPLE 5 meBPEA Stabilization of 1-chloro-3,3,3 trifluoropropene

Two 100 mL jars were filled each with 38.4 g of 1-chloro-3,3,3-trifluoro-1-Propene and 3 g of either Polycat™ 5 (pentamethylated diethylenetriamine; Air Products) or meBPEA respectively. Both jars were sealed and hand shaken for 30 sec. Almost immediately, the Polycat™ 5 solution generated a cloudy white precipitate, reflecting incompatibility of the Polycat™ 5 amine catalyst with the hydrochlorofluorocarbon in mixture. The meBPEA remained clear for the initial 2.5 h. After standing overnight at room temperature, the Polycat™ 5 solution had become more colored in nature, with a dark ring formed around the surface of the jar/solution interface, whereas the meBPEA had only a white cloudiness to its appearance, reflecting compatibility of the meBPEA catalyst with the hydrochlorofluorocarbon in mixture.

What is claimed is:

1. A composition comprising:
   (a) a cyclic amine of Formula I:

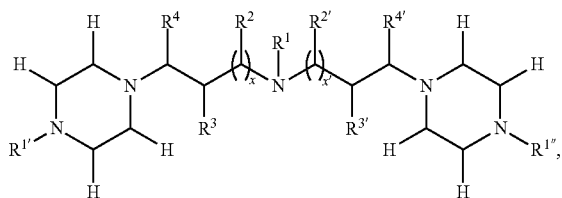

or of Formula II:

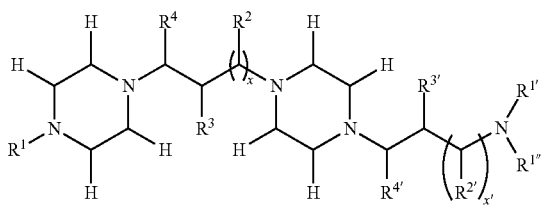

where, in Formula I and II, $R^1$, $R^{1'}$, and $R^{1''}$ are independently selected from hydrogen and C1-C8 hydrocarbyl groups, wherein at least one of $R^1$, $R^{1'}$, or $R^{1''}$ is a C1-C8 hydrocarbyl group; where $R^2$, $R^{2'}$, $R^3$, $R^{3'}$, $R^4$, and $R^{4'}$ are independently selected from hydrogen, —CH$_3$, and —CH$_2$CH$_3$; and x and x' are independently 0 or 1; or an acid blocked cyclic amine of Formula I or II where any one or more of the nitrogens in Formula I or II carry a positive charge and are electrostatically blocked by an acid anion;
   (b) a polyol; and
   (c) a polyisocyanate.

2. The composition of claim 1 further comprising a hydrofluorochlorocarbon or a hydrofluorocarbon.

3. A composition comprising:
   (a) a cyclic amine of Formula I:

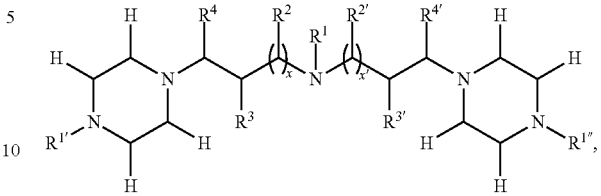

or of Formula II:

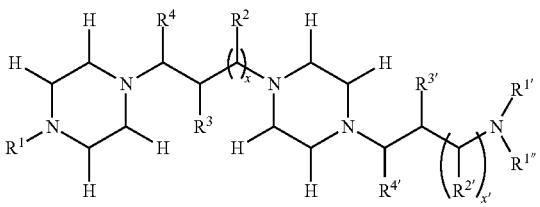

where, in Formula I and II, $R^1$, $R^{1'}$, and $R^{1''}$ are independently selected from hydrogen and C1-C8 hydrocarbyl groups, wherein at least one of $R^1$, $R^{1'}$, or $R^{1''}$ is a C1-C8 hydrocarbyl group; where $R^2$, $R^{2'}$, $R^3$, $R^{3'}$, $R^4$, and $R^{4'}$ are independently selected from hydrogen, —CH$_3$, and —CH$_2$CH$_3$; and x and x' are independently 0 or 1; or an acid blocked cyclic amine of Formula I or II where any one or more of the nitrogens in Formula I or II carry a positive charge and are electrostatically blocked by an acid anion; and
   (b) a hydrofluorochlorocarbon or hydrofluorocarbon.

4. The composition of claim 1, where, in Formula I or II, at least one of $R^1$, $R^{1'}$, or $R^{1''}$ is a C1-C3 hydrocarbyl group.

5. The composition of claim 1, where, in Formula I or II, $R^1$, $R^{1'}$, and $R^{1''}$ are independently selected from —CH$_3$, —CH$_2$CH$_3$, —CH$_2$CH$_2$CH$_3$, —CH(CH$_3$)$_2$, —CH(CH$_3$)CH$_2$CH(CH$_3$)$_2$, and —CH$_2$CH(CH$_2$CH$_3$)CH$_2$CH$_2$CH$_2$CH$_3$.

6. The composition of claim 5, where, in Formula I or II, $R^1$, $R^{1'}$, and $R^{1''}$ are —CH$_3$.

7. The composition of claim 2 wherein the hydrofluorochlorocarbon or hydrofluorocarbon is selected from the group consisting of chlorodifluoromethane; 1-chloro-1,1-difluoroethane; 1,1-difluoroethane; 1,2-difluoroethane; 1,1,1,2-tetrafluoroethane; 2,2-dichloro-1,1,1-trifluoroethane; 1,2,2-trifluoroethane; 1,1,1,2,3,3,3-heptafluoropropane; 1,1,1,3,3-pentafluoropropane; 1,2-dichloro-3,3,3-trifluoropropene; 1-chloro-1,3,3,3-tetrafluoropropane; 1-chloro-3,3,3 trifluoropropene; cis-1,3,3,3-tetrafluoropropene; 1,2,2,3,3-pentafluoropropane; 1,1,1,3,3-pentafluorobutane; and 1,1,2,2-tetrafluoroethyl methyl ether.

8. The composition of claim 7 wherein the hydrofluorochlorocarbon is 1-chloro-3,3,3 trifluoropropene.

9. A polyurethane foam derived from the composition of claim 1.

10. A method for preparing a polyurethane foam comprising providing the composition of claim 1 and reacting the polyol and the polyisocyanate in the presence of the cyclic amine of Formula I or II, or the acid blocked cyclic amine of Formula I or II.

11. The composition of claim 1 wherein the cyclic amine of Formula I is methyl-bis-[2-(4-methyl-piperazin-1-yl)- ethyl]-amine (meBPEA), or the cyclic amine of the Formula II is dimethyl-(2-{4-[2-(4-methyl-piperazin-1-yl)-ethyl]-piperazin-1-yl}-ethyl)-amine.

12. The composition of claim 3, where, in Formula I or II, at least one of $R^1$, $R^{1'}$, or $R^{1'''}$ is a C1-C3 hydrocarbyl group.

13. The composition of claim 3 wherein the hydrofluorochlorocarbon or hydrofluorocarbon is selected from the group consisting of chlorodifluoromethane; 1-chloro-1,1-difluoroethane; 1,1-difluoroethane; 1,2-difluoroethane; 1,1,1,2-tetrafluoroethane; 2,2-dichloro-1,1,1-trifluoroethane; 1,2,2-trifluoroethane; 1,1,1,2,3,3,3-heptafluoropropane; 1,1,1,3,3-pentafluoropropane; 1,2-dichloro-3,3,3-trifluoropropene; 1-chloro-1,3,3,3-tetrafluoropropane; 1-chloro-3,3,3 trifluoropropene; cis-1,3,3,3-tetrafluoropropene; 1,2,2,3,3-pentafluoropropane; 1,1,1,3,3-pentafluorobutane; and 1,1,2,2-tetrafluoroethyl methyl ether.

14. The composition of claim 3 wherein the cyclic amine of Formula I is methyl-bis-[2-(4-methyl-piperazin-1-yl)-ethyl]-amine (meBPEA), or the cyclic amine of the Formula II is dimethyl-(2-{4-[2-(4-methyl-piperazin-1-yl)-ethyl]-piperazin-1-yl}-ethyl)-amine.

* * * * *